Figure 1:
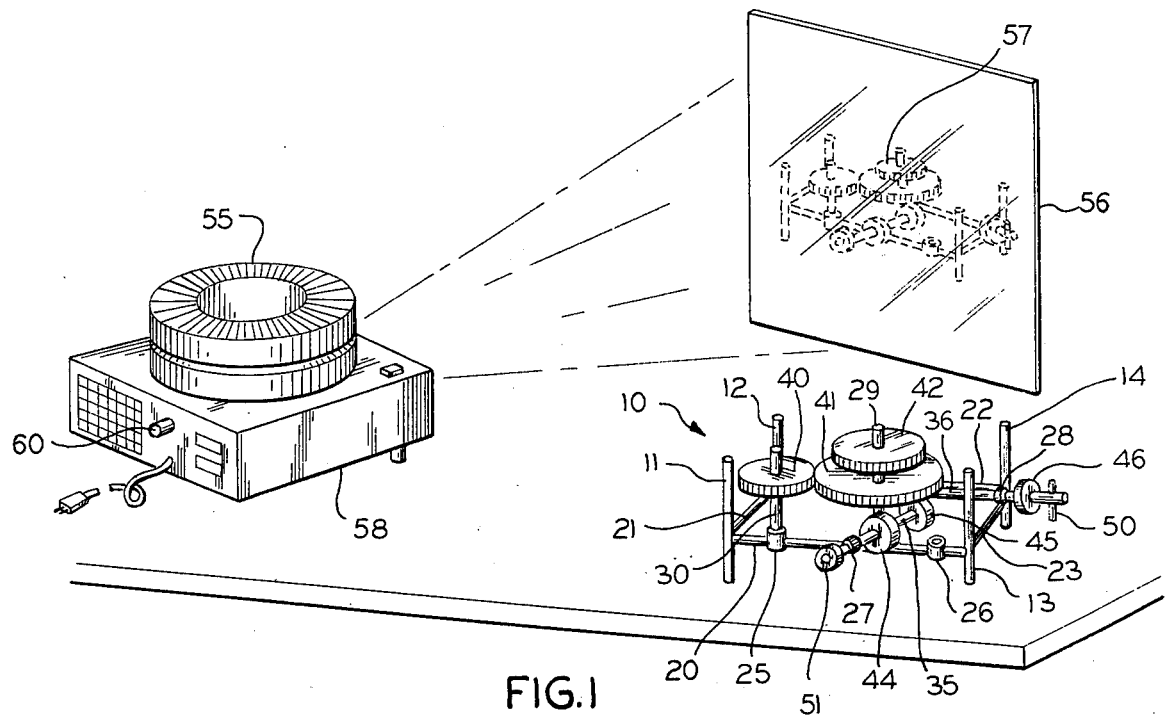

United States Patent [19]

Hester

[11] 4,014,108
[45] Mar. 29, 1977

[54] VISUAL PERCEPTION TESTING METHOD

[75] Inventor: Edward J. Hester, Chicago, Ill.

[73] Assignee: Goodwill Industries of Chicago and Cook County, Chicago, Ill.

[22] Filed: Nov. 5, 1975

[21] Appl. No.: 628,920

[52] U.S. Cl. .................................................. 35/13
[51] Int. Cl.$^2$ ....................................... G09B 25/02
[58] Field of Search ............ 35/8 R, 10, 13, DIG. 3

[56] References Cited

UNITED STATES PATENTS

| 2,682,117 | 6/1954 | Wales | 35/13 UX |
| 3,276,149 | 10/1966 | Barnabas | 35/13 UX |
| 3,391,473 | 7/1968 | Hays | 35/13 |
| 3,412,480 | 11/1968 | Connell | 35/DIG. 3 |
| 3,646,592 | 2/1972 | Bosley et al. | 273/157 R X |

OTHER PUBLICATIONS

Montgomery Ward, 1974 Christmas Catalog; received Oct. 1974, p. 190 relied on.

Primary Examiner—Anton O. Oechsle

[57] ABSTRACT

A perception testing method and apparatus provides an extremely simple machine-like structure made of modular parts, a projector, and a series of transparencies or slide pictures. The modular parts may be assembled or disassembled in any of many different combinations or modifications to provide a great variety of "machines." Slide pictures are taken from many angles of each of these combinations or modifications. Then, one of these many combinations is physically placed in front of a subject being tested, and a series of slide pictures is projected on a screen near the physical combination. The subject must decide whether the physical structure and each picture are identical or are different.

2 Claims, 6 Drawing Figures

U.S. Patent  Mar. 29, 1977  4,014,108

VISUAL PERCEPTION TESTING METHOD

This invention relates to methods of testing the perception of a subject under test and more particularly — although not exclusively — to a method of conducting vocational testing.

Vocational testing includes an appraisal of many skills, one of the most important of which is perception or interpretation of physical sensations. This perception may vary with a great variety of different skill levels. For example, one skill level is required to see fairly obvious similarities and differences between two identical views of same items. Another skill level is required to see such similarities and differences when the same item is viewed from many different angles and perspectives or when the differences are subtle or varied.

Accordingly, an object of the invention is to provide a method of testing visual perception over a wide range of skill levels and with a high degree of accuracy. Here, an object is to provide a method of testing visual preception over a range extending from simple and direct comparison to an almost intuitive judgment.

Another object of the invention is to provide a method utilizing very low cost, commonly available, easy to use devices for testing visual perception. Here, an object is to provide a method utilizing apparatus which may be used on either a custom basis (whereby the tester may select his own presentation of subject matter) or on a preselected basis (whereby the tester merely buys a presentation kit of testing subject matter).

In keeping with an aspect of this invention, a perception testing method provides an extremely simple machine-like structure of modular parts which may be assembled in any of many different ways to provide a great variety of slightly different "machines". For example, children's construction toys may be used to provide the modular parts. Slide transparencies or pictures are taken from many angles of each of these combinations. Then, one of the many combinations is physically placed within the sight and view of a subject, who is being tested. Many slide pictures are projected on a screen near the physical combination, and the subject decides whether each picture is the same as or different from the physical structure which he sees. He may also be required to identify the differences, if any.

The nature of a preferred embodiment of the invention may become more apparent from a study of the attached drawing, wherein:

FIG. 1 shows the inventive combination of a projector, a screen, and a modular machine; and FIGS. 2–6 are a number of similar views of the same machine, slightly modified, in each case.

According to the invention, an extremely simple, modular machine is adapted to be assembled in any of many different ways. The nature of the modules is not too important. They may be custom built or they may be taken from construction toys. For example, four parts 11–14 may have any suitable connectors for receiving the ends of various strut members 20–23 so that a complete frame may be constructed simple by fitting parts together. Any suitable number of sockets 25–28 may be fitted over the struts and turned to a vertical or horizontal position. A vertical post 29, 30 may be fitted into anyone or more of these sockets. Likewise, horizontal shafts 35, 36 may be fitted into other sockets. Gears 40–42 may be fitted on over the vertical shafts 29, 30. Wheels 44–46 may be fitted over the horizontal shafts 35, 36. A handle 50 may be placed on the end of shaft 36 and a knob 51 on shaft 35. In this manner, the simple machine 10 may be constructed quickly and easily.

Figure 2:
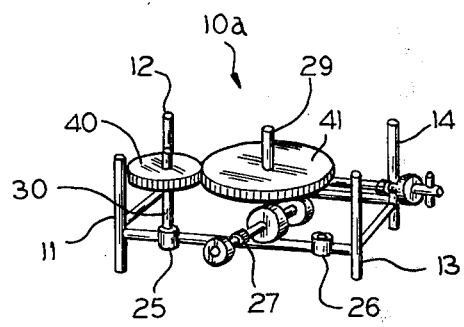

The machine 10 of FIG. 1 may be built in many other forms or modified. For example, the machine 10a of FIG. 2 is identical to that of FIG. 1 except that the gear 42 has been removed from shaft 29.

Figure 3:
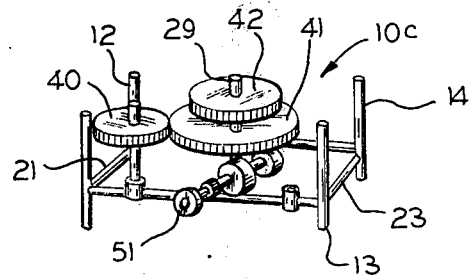

The machine 10b of FIG. 3 is the same as the machine 10 of FIG. 1 except that shaft 30 and gear 40 have been moved from socket 25 to 26.

Figure 4:
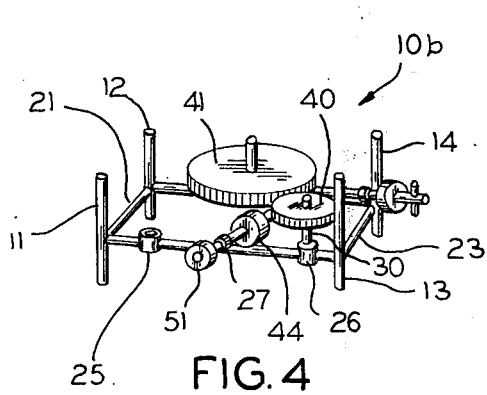

The machine 10c of FIG. 4 is the same as the machine 10 of FIG. 1 except that socket 28, horizontal shaft 36, wheel 46, and handle 50 have been removed from strut 23.

Figure 5:
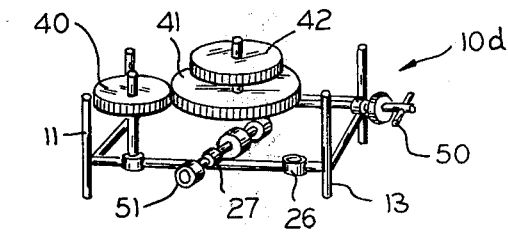

The machine 10d of FIG. 5 is the same as the machine 10 of FIG. 1 except that the handle 50 has been turned by 90°.

Figure 6:
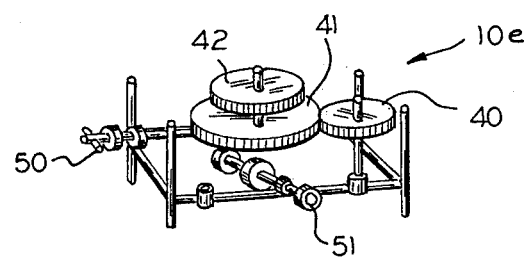

The machine 10e of FIG. 6 is a mirror image of the machine 10 of FIG. 5, and otherwise identical.

It should be apparent that many other modifications may also be provided by further moving or turning the modular parts. In addition, the entire machine could originally have been constructed in some other manner. For example, gears 40–42 and wheels 44–46 or knob 51 and handle 50 could have been interchanged. More or less gears and wheels, or shafts and posts could have been added to the original machine 10. Likewise, colored wheels or gears could be provided or changed. Hence, it seems that an extremely great variety of machines and modified machines may be provided quickly and easily.

The next step in the inventive process is to photograph both the original and the modified machines from many different angles. These photographs are then assembled and stored in a magazine 55 (FIG. 1) in an order which is selected according to the goals of the testing program.

The original machine 10 is physically placed before a person who is being tested while images 57 of the slides or photographs are projected onto a screen 56 from a projector 58.

The person who is being tested must compare each of the projected images 57 with the physical structure. Depending upon how the test is structured, the tested person must then mark his paper with either a "same" or "different" depending upon whether image 57 is the same as or different from the physical machine 10. Or, he may be required to either mark same or identify the differences.

In addition, a timer 60 may be adapted to change the projected image 57 after it has been displayed for a definite period of time, so that the person being tested must reach a decision within that time period. If desired, the timer may also be constructed to have a variable time cycle, which can be selected. Or, a progressive time period may be built into the testing program. For example, the projected image 57 may be changed at progressively shorter time intervals, so that a learning curve is built into the test.

Hence, it should now be apparent that the invention provides for a great variety of test comparisons at a great variety of different skill levels.

Various changes and modifications may be made by those who are skilled in the art. Therefore, the appended claims are to be construed to cover all equivalent structures.

I claim:

1. A method of conducting tests for visual perception comprising the steps of:
  a. building a machine from modular parts which may be added, removed, or changed to alter the physical appearance of said machine;
  b. photographing said machine in each of its altered physical appearances and from a plurality of different angles and view points,
  c. setting said machine in one physical form adjacent a screen in view of the person being tested and
  d. projecting said photographed pictures on said screen in timed succession, whereby the person being tested must determine whether each projected picture depicts the same physical form or a different form that the adjacent machine.

2. The method of claim 1 wherein said step (d) comprises the added step of varying the succession time between the photographed pictures to construct a learning curve.

* * * * *